United States Patent [19]
Dewey

[11] Patent Number: 5,548,352
[45] Date of Patent: Aug. 20, 1996

[54] ANTI-ASTIGMATIC OPHTHALMIC CONTACT LENS FOR USE IN PERFORMING LASER SURGERY

[75] Inventor: David A. Dewey, Sunnyvale, Calif.

[73] Assignee: Coherent, Inc., Santa Clara, Calif.

[21] Appl. No.: 183,530

[22] Filed: Jan. 19, 1994

[51] Int. Cl.$^6$ ................................................. G02C 7/04
[52] U.S. Cl. ........................ 351/160 H; 351/177; 351/219
[58] Field of Search ......................... 351/160 H, 160 R, 351/161, 162, 177, 219

[56] References Cited

U.S. PATENT DOCUMENTS

| | | | |
|---|---|---|---|
| 4,378,147 | 3/1983 | Fujita | 351/205 |
| 4,506,962 | 3/1985 | Roussel | 351/160 R |
| 4,598,984 | 7/1986 | Rol | 351/219 |
| 4,664,490 | 5/1987 | Rol | 351/219 |
| 5,252,998 | 10/1993 | Reis et al. | 351/160 R |

FOREIGN PATENT DOCUMENTS

| | | |
|---|---|---|
| 0059159A1 | 2/1982 | Canada . |
| 0150779A3 | 1/1985 | France . |
| 0161645A1 | 5/1985 | France . |
| 1731157A1 | 4/1989 | U.S.S.R. . |

OTHER PUBLICATIONS

One-page advertisement, "1 CGA Contact Lens for the Chamber Angle" and 1 CGI Contact Lens for the Iris, *LASAG Laser Contact Lenses*.

One-page advertisement, "CGA, CGI, CGP, CGV, 1 CGA, 2 CGI, 3 CGP, 4 CGV," by *LASAG Laser Contact Lenses*. *Ocular Instruments Product Catalog*, containing excerpts, "Argon Lenses" and YAG Laser Lenses, 1992, pp. cover, 7–8 & 11.

Two-page advertisement, "Contact Lenses: Optimal for every purpose," by *Rodenstock*.

Booklet, *Contact Glasses*, "Acrylic Contact Lenses for Diagnostic Purposes," *Haag–Streit AG*, pp. 4–7.

Chapter 3.5, "Gonioscopy," *Ocular Examination With the Slit Lamp*, by *Zeiss*, pp. cover & 31.

*Primary Examiner*—Scott J. Sugarman
*Attorney, Agent, or Firm*—Limbach & Limbach

[57] ABSTRACT

A contact lens for viewing the interior of a patient's eye during an argon laser trabeculoplasty (ALT) procedure and for delivering laser energy to desired regions of the trabecular meshwork of the eye. The contact lens is fabricated from a hollow plastic body which is filled with a medium having an index of refraction which is substantially the same as that of the aqueous humor within a patient's eye. Visible and laser light enter the lens by means of a thin window of substantially uniform thickness and exit the lens (thereby entering the eye) at a front face of substantially uniform thickness whose outer curvature is approximately the same as that of the patient's eye. The degree of astigmatic focusing which normally occurs as the visible light and laser beam pass through the contact lens and cornea and into the aqueous humor is substantially reduced. This assists the surgeon performing the procedure to better view the interior of the eye and to place a better defined laser spot on the desired regions of the trabecular meshwork.

28 Claims, 4 Drawing Sheets

5,548,352

ANTI-ASTIGMATIC OPHTHALMIC CONTACT LENS FOR USE IN PERFORMING LASER SURGERY

TECHNICAL FIELD

The present invention is generally directed to methods of reducing intraocular pressure in patients having glaucoma by means of argon laser trabeculoplasty, and more specifically, to a contact lens used to view the interior of a patient's eye during the procedure which corrects for the astigmatic focusing caused by the difference in refractive index between the contact lens material and the aqueous humor of the eye.

BACKGROUND OF THE INVENTION

Glaucoma is a disease of the eye which reduces the field of view of the afflicted person slowly over time. Glaucoma is believed to be associated with an elevated pressure in the eye, although the exact cause of the disease is not known at this time. This possible explanation for the cause of glaucoma, and the structure of the eye itself, will be described with reference to FIG. 1, which is a side view of a human eye 50 and shows its primary internal components.

Light enters eye 50 through the cornea 55. The light passes through the interior of eye 50 and is focused by the lens 53 onto the retina 59 at the back of the eye. The iris 58 acts as an aperture for lens 53 and serves to define the pupil 51, which is that portion of lens 53 not covered by iris 58. Lens 53 serves to divide the interior of eye 50 into the posterior chamber 54 and the anterior chamber 56.

In a normal (non-diseased) eye, the pressure within eye 50 is maintained at a moderate level by an equilibrium between the production of aqueous humor 52 within eye 50 and its discharge from eye 50. Aqueous humor 52 is a fluid contained within eye 50 which is produced by the ciliary body 60 located behind iris 58.

Aqueous humor 52 is secreted by ciliary body 60 of eye 50 and flows around lens 53 to pupil 51. The fluid circulates through pupil 51 into anterior chamber 56, flowing around iris 58 into the "angle" 57 of the eye between iris 58 and cornea 55. Aqueous humor 52 is discharged from anterior chamber 56 through absorption by the sinus venous or canal of Schlemm (not shown), eventually being discharged from eye 50. A thin filtering system known as the trabecular meshwork (not shown) is located in "angle" 57. The trabecular meshwork controls the rate at which aqueous humor 52 flows out of anterior chamber 56 and is absorbed by the sinus venous. In a healthy eye, the trabecular meshwork allows aqueous humor 52 to flow out of anterior chamber 56 at a controlled rate, one that matches the rate at which it is produced by ciliary body 60.

As a person ages, the trabecular meshwork may become less able to pass aqueous humor at the desired rate. As a result, the pressure within the eye can become elevated because aqueous humor 52 is produced at a greater rate by ciliary body 60 than the rate at which it flows out of anterior chamber 56 and is discharged from eye 50. Such a condition is believed to cause glaucoma.

One method of treating a person with glaucoma (high intraocular pressure) is to apply eye drops containing a medication which reduces the pressure within the eye. However, when this treatment is not satisfactory, argon laser trabeculoplasty may be used.

Argon laser trabeculoplasty (ALT) is a procedure in which a series of approximately fifty (50) laser burns having a spot size of fifty microns (50 μm) in diameter are placed around a one hundred and eighty (180) degree region of the trabecular meshwork. The meshwork itself is only about one hundred microns (100 μm) wide and is viewed by the surgeon through a mirrored contact lens which enables the surgeon to view the trabecular meshwork and to properly place the laser beam. The laser burns are made in the "angle" of a patient's eye, the region between the cornea and iris. ALT is believed to work by opening up the trabecular meshwork so that the rate at which aqueous humor flows out of the anterior chamber of the eye is increased. This serves to reduce the intraocular pressure and prevent loss of vision.

FIG. 2 shows the components of a typical retinal photocoagulator laser system 10 used to perform a surgical procedure such as ALT on a patient's eye. Such a system is described in U.S. Pat. No. 5,171,242, issued Dec. 15, 1992, which has a common inventor and is assigned to the same assignee as the present application.

Laser system 10 includes a laser means 12 for generating a beam of laser radiation having a wavelength and intensity suitable for the desired procedure. Laser means 12 is comprised of a suitable laser 14 and a laser control means 16. Laser control means 16 receives power from any suitable outside energy source and delivers it in a controlled fashion to laser 14. Lasers means suitable for ophthalmological therapies generally, and laser trabeculoplasty therapies in particular, are Coherent laser consoles which provide both lasers and laser control means and include Coherent's Novus 2000, as well as Coherent's Argon laser console model no. 920 A and Argon-Krypton laser console model no. 920 A/K.

Laser means 12 is coupled to a laser focusing means 20 by laser transmission means 18. Laser transmission means 18 is generally an optical fiber cable, although any suitable wave guide capable of efficient transmission of laser radiation at desired wavelengths can be used.

Laser focusing means 20 controls the spot size and focus mode of the laser radiation generated by laser means 12. Laser focusing means 20 may be comprised of any system of lenses, mirrors or other construction capable of focusing laser radiation. It is preferred to construct laser focusing means 20 in the form of a lens system with an adjustable focal length to permit the spot size of the laser radiation at the target to be varied.

Optical means 24 for receiving and delivering laser radiation to the eye is coupled to laser focusing means 20. In laser system 10 of FIG. 2, optical means 24 is provided with a first mirror 26 for receiving laser radiation from laser focusing means 20 and delivering it to the eye. Optical means 24 is also provided with a source of visible light 28. Light generated by source 28 is received by second and third mirrors 30 and 32 which reflect the visible light to the eye, thereby providing the illumination necessary for the physician to view the interior of the eye and position the laser radiation.

Magnification means 40 is coupled to optical means 24 opposite the eye to permit the physician to view the trabecular meshwork in greater detail in order to properly position the laser radiation during therapeutic treatment. A suitable magnification means would be a microscope having magnifying capacity suitable for enlargement of the trabecular meshwork. The combination of magnifying means 40 and optical means 24 is frequently referred to collectively as a "slit lamp" by those skilled in the art.

In addition to the apparatus just described, it is necessary for the physician to employ a form of a contact lens 41 to make it possible for the physician to focus an image of the trabecular meshwork. Normally the structure of the eye, in particular the action of cornea 55 of eye 50 shown in FIG. 1, interferes with the physician's ability to see an image of the meshwork. Because the index of refraction of the inside of the eye is greater than that of air, the steeply angled light rays coming from the "angle" of the eye between the cornea and iris are subject to total internal reflection at the cornea/ air interface and cannot escape from the eye. A contact lens is therefore used to provide an index matching (or higher index) material at the interface in order to allow the light rays to escape the eye. The contact lens is mirrored to permit the laser beam and light from a visible light source to enter the eye at the steep angles necessary to illuminate the "angle" of the eye.

Contact lens 41 is placed between optical means 24 and the eye. Contact lens 41 is positioned so that it is in contact with cornea 55 through a gel which is placed on the contact lens by the physician. Examples of typical contact lens systems used in conjunction with retinal photocoagulator laser systems for performing ALT procedures are the CGA lens manufactured by Lasag, the Ritch trabeculoplasty laser lens, single and two mirror Gonio laser lenses and Trokel F/3 Gonio laser lens manufactured by Ocular Instruments, Inc., and the RGO Gonio lens manufactured by Rodenstock.

FIG. 3 shows a typical contact lens 41 of the type used in an ALT procedure and its placement over a patients' eye 50 in order to focus visible and laser light into the "angle" of the eye.

Contact lens 41 has a main body 43 having a front face 44 which is placed over eye 50 during the procedure and a flat surface 46 which permits visible and laser light to enter lens 41. Front face 44 has a transmissive portion which allows light to exit lens 41. The outer curvature of front face 44 is similar to that of cornea 55, so that lens 41 fits snugly over a patient's eye. Lens 41 may be fabricated so as to have one or more magnification lenses 48 external to lens body 43, which are placed on various regions of surface 46. Magnification lenses 48 allow the surgeon performing the ALT procedure to obtain an enlarged view of the inside of eye 50. The interior 45 of lens 41 is solid and is substantially transparent to the visible and laser light used in the procedure. Lens 41 has one or more mirrored surfaces 42 positioned in its interior on the inner wall of main body 43. Mirrored surfaces 42 serve to direct visible and laser light which enters lens 41 through surface 46 to the desired region of eye 50.

As mentioned, laser and visible light enters contact lens 41 by means of surface 46. The light may enter lens 41 and be viewed by the surgeon through magnification lens 48, if needed, to improve the image. The light propagates through the substantially transparent interior 45 of lens 41 and reflects off of mirrored surface 42. As indicated in FIG. 3, reflected light rays 80 are steeply angled in order to exit lens 41 at front face 44 and then enter eye 50 at an appropriate angle to illuminate the region of eye 50 in which the trabecular meshwork is located. As an example, during an ALT procedure, light rays 80 typically enter eye 50 at an angle in the range of 50 to 80 degrees to a normal, N, to the surface of cornea 55 of eye 50.

When a light beam passes from one medium to another across a curved surface it is caused to come to a focus because of the difference in the refractive indices of the media. However, if the visible light or laser beam crosses the surface at a steep angle it becomes astigmatically focused, i.e., the focal points of the light beam are different in the sagittal (horizontal) and tangential planes. This leads to a degradation of the image. Astigmatic focusing is undesirable because it reduces image clarity and increases the spot size of the focused laser beam, and therefore can create problems during procedures such as ALT which require precise placement and size of the laser beam.

In a typical ALT contact lens the visible light and laser beam cross two curved surfaces, one between the body of the contact lens and the cornea, and a second between the cornea and the aqueous humor. The visible light and laser beam must cross the surfaces at a steep angle in order to focus into the narrow "angle" between the cornea and iris of a patient's eye. Since the refractive indices (n) of the lens (typically made of plastic, having n=1.48), cornea (n=1.38), and aqueous humor (n=1.34) differ, astigmatic focusing is a natural result of the geometry of the system.

The problem of astigmatic focusing has been recognized by manufacturers of contact lenses used in ALT procedures. Ocular Instruments, Inc. of Bellevue, Wash., produces a Trokel F/3 Gonio Laser Lens which is designed to correct for cornea induced astigmatism. This lens has an appropriately angled, curved front surface which serves to introduce a compensating astigmatism (one of the opposite sign) in order to cancel the astigmatism introduced by the exit face. A disadvantage of this means of correcting for cornea induced astigmatism is that the degree of compensation depends on the angle at which light enters the lens, so that the effectiveness of the lens in reducing astigmatism can vary.

The contact lens typically used in an ALT procedure is a solid body made of glass or plastic. These materials result in a contact lens having an index of refraction which is higher than the optimal value, but the solid body allows mirrors to be conveniently mounted or fabricated on it. A plastic lens has the added benefit of being lighter weight and less fragile than a glass lens. Since the index of refraction of most glass or plastic lenses (n=1.45 to 1.55) is greater than that of the aqueous humor of the eye, the laser beam becomes astigmatically focused as it passes from the contact lens into the eye. This problem can be partially addressed by tilting the contact lens to produce a compensating astigmatism. However, the direction and degree of tilting is often limited by practical considerations, such as the patient's facial features.

ALT is a procedure where a small laser spot is important. As the trabecular meshwork is only 100 µm across, it is desirable to make the laser burn in it as small and clean as possible. A clean 50 µm spot, which is the smallest typically obtainable, is obtained in a photocoagulator by converging the laser beam at a relatively steep angle. Astigmatic focusing can increase the spot size from 50 µm to 90 µm or more. Even if a reducing section of the contact lens is used, which can be obtained by the addition of a "button" lens, the spot size may still be increased to as much as 75 µm. It is apparent that reducing the degree of astigmatic focusing would provide better viewing of the area to be treated and a smaller laser spot size, and hence a more effective and safer procedure for treating glaucoma.

What is desired is a contact lens for use in viewing the interior of the eye and delivering laser energy during an ALT procedure which causes less astigmatic focusing of the laser beam than contact lenses typically used in such procedures.

SUMMARY OF THE INVENTION

The present invention is directed to a contact lens for use in viewing the trabecular meshwork of a patient's eye during an ALT procedure, and for delivering laser energy to desired regions of the meshwork. The contact lens of the present invention is fabricated from a thin-walled, hollow body which is filled with a fluid or medium having an index of refraction which is substantially the same as the aqueous humor inside a person's eye. Water is an example of such a fluid or medium. Laser and visible light enters the lens through a flat window, travels through the medium, is reflected from an internal mirror and then exits the lens (thereby entering the eye) through a curved window whose outside curvature is approximately the same as that of a patient's eye.

Since the index of refraction of the fluid or medium is approximately equal to that of the aqueous humor contained within the eye, the degree of astigmatic focusing which normally occurs as the laser beam passes from a solid plastic contact lens into the cornea and then into the aqueous humor is substantially reduced. This assists the surgeon performing the procedure to more clearly view the interior of the eye and to place a better defined laser spot on the desired regions of the trabecular meshwork.

Further objects and advantages of the present invention will become apparent from the following detailed description and accompanying drawings.

DETAILED DESCRIPTION OF THE PREFERRED EMBODIMENT

The inventor of the present invention has recognized that if the type of contact lens normally used in an ALT procedure were replaced with a lens having an index of refraction closer to that of the aqueous humor of the eye, then the total astigmatism of the contact lens-eye system could be reduced. This is because the astigmatism created when the light passes from the lens body into the cornea would be nearly equal in size, but opposite in sign to that caused by the light passing from the cornea into the aqueous humor. In such a case, the total astigmatism would be nearly zero.

Since water has an index of refraction of n=1.33, it is almost perfectly index matched to the aqueous humor. However, a lens made entirely of water is not practical since without some type of container, a fluid will not hold a desired shape. However, a thin-walled, hollow plastic lens filled with water or another suitable medium is practical and would produce similar results. The total astigmatism created when light passes from water through a thin, uniform cross-section (thickness) spherical surface into the spherically curved cornea and then into the aqueous humor would be only a fraction of that generated when using a conventional ALT lens.

Figure 1:
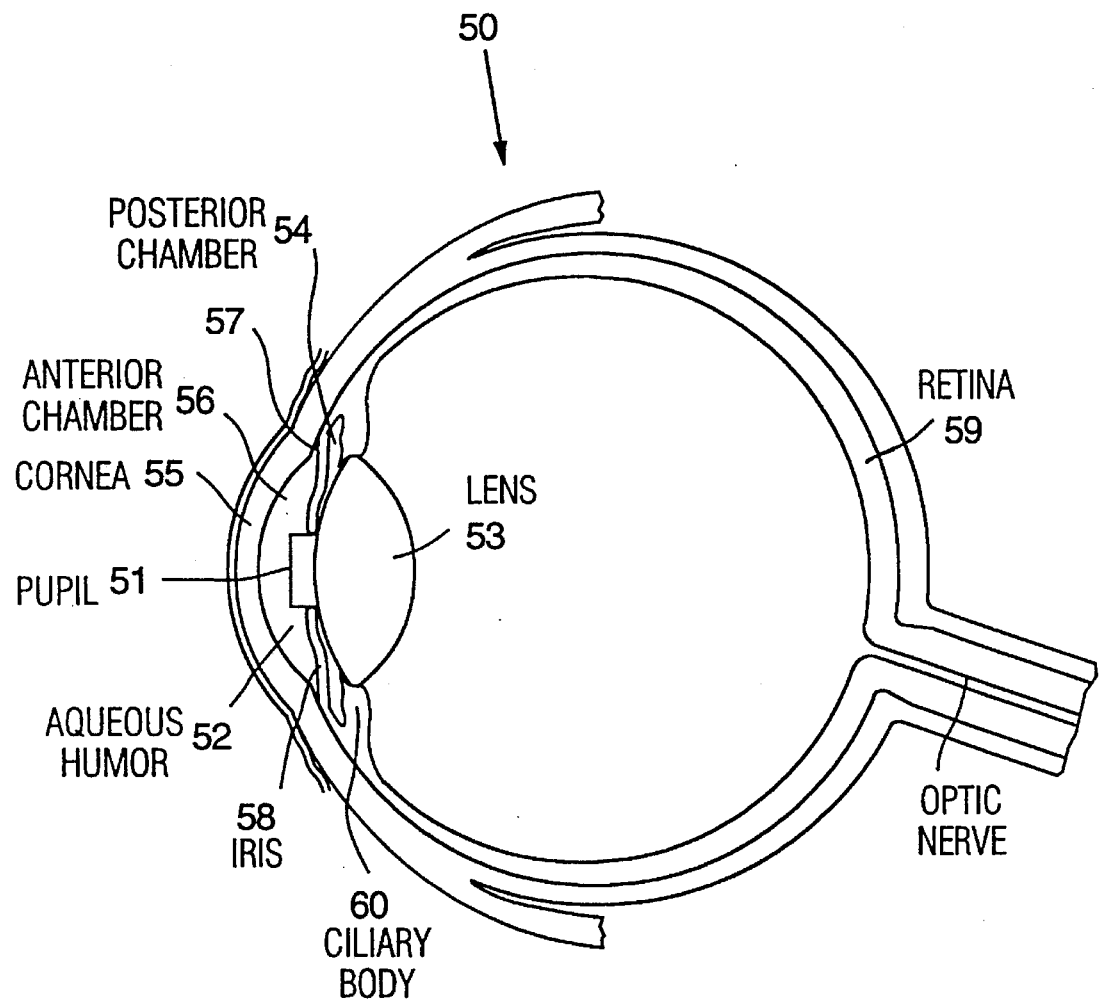
FIG. 1 is a side view of a human eye and shows its primary internal components.
Figure 2:
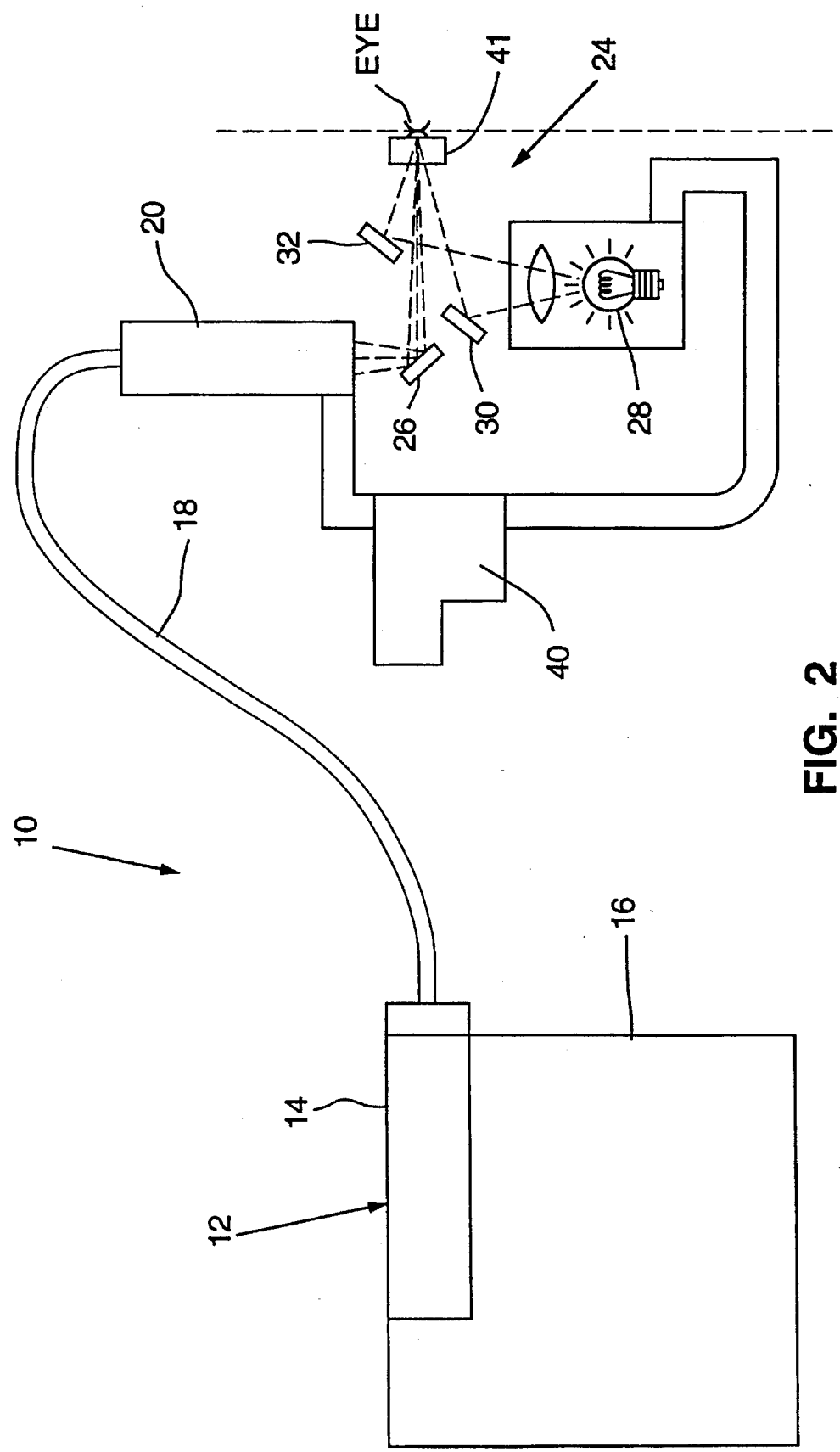
FIG. 2 shows the components of a typical system used to deliver laser light to a patient's eye during an argon laser trabeculoplasty (ALT) procedure.
Figure 3:
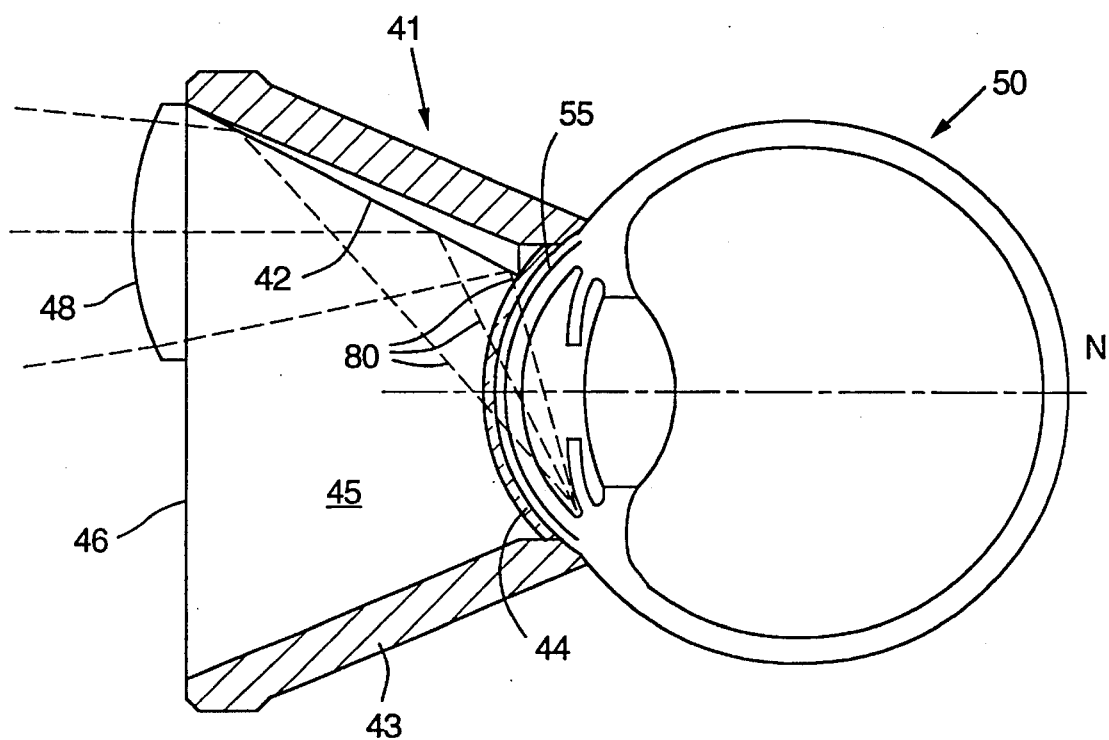
FIG. 3 shows a typical contact lens used in an ALT procedure and how laser light is focused into a patient's eye.
Figure 4:
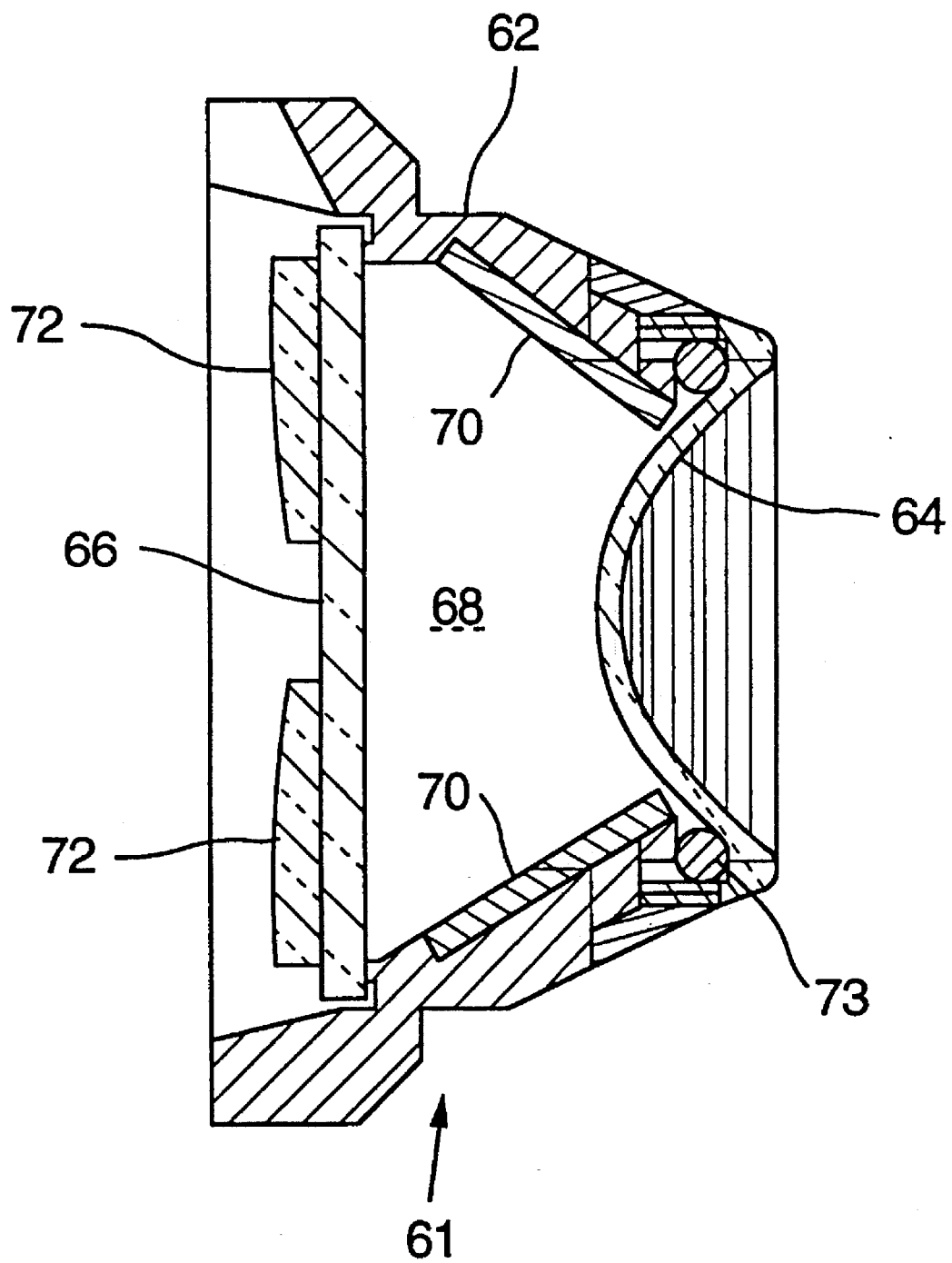
FIG. 4 is a cut-away side view of the anti-astigmatic contact lens of the present invention.

FIG. 4 is a cut-away side view of the anti-astigmatic contact lens 61 of the present invention. Lens 61 includes a lens body 62 which has thin walls and is hollow. Lens front 64 has an external curvature which is substantially the same as that of a patient's eye (not shown) and is oriented so that lens 61 can fit over the eye. Lens front 64 has a finite thickness and for purposes of analyzing the astigmatic focusing it contributes, it can be treated as two spherical surfaces (an external one which mates to the eye and an internal one which light passes through in going from the interior of lens 61 through lens front 64) bounding a curved wall composed of the material from which lens front 64 is fabricated. Lens front 64 includes a transmissive portion which is substantially transparent to visible light and to laser light at the wavelength(s) used for the surgical procedure for which lens 61 is to be used.

Visible and laser light enters lens 61 through a substantially transparent flat window 66. In a preferred embodiment of the invention, the hollow interior of lens body 62 is filled with water 68. This is done prior to sealing window 66 to lens body 62 if lens body 62 and window 66 are fabricated as separate parts.

A fluid or medium other than water may be used, as long as it is sufficiently transmissive to visible and laser light at the desired wavelength(s) and has substantially the same index of refraction as the aqueous humor within a patient's eye. In addition, the medium chosen should be one which is capable of remaining clear during the use of contact lens 61, and thus should not be one in which algae or fungus can easily grow. Thus, depending upon the medium used, a sterilizing agent (such as alcohol) may need to be added to prevent the growth of algae or fungus. Another example of a suitable medium which can be used to fill the inside of lens body 62 is a hydrophilic material such as the hydrophilic polymers used to form soft contact lenses. The index of refraction of the fluid or medium used to fill the hollow interior of lens body 62 should be in the range of 1.25 to 1.45, and is preferably in the range of 1.32 to 1.35.

Mirrors 70 are affixed to or fabricated on the interior sides of lens body 62 and permit the surgeon performing the ALT procedure to view the trabecular meshwork of the eye and deliver the laser light to its desired target. Window 66 may be sealed to lens body 62 by means of a silicone glue. Magnification lens(es) 72 may be affixed at desired locations to the outside of window 66 to permit the surgeon to have a magnified view of the work area. If magnification lenses are used, they should cover only a portion of the surface area of window 66.

As previously mentioned, when visible or laser light enters contact lens 61 through window 66, it encounters a medium having an index of refraction close to that of the aqueous humor of the eye. The light is reflected by mirror 70 so that it will traverse lens front 64 at an appropriate angle to illuminate the desired region of a patient's eye. The light undergoes a first astigmatic focusing upon passing through the internal spherical surface of lens front 64 at this steep angle. The light undergoes a second astigmatic focusing upon passing through the external spherical surface of lens front 64 and entering the curved spherical surface of the patient's cornea, and a third astigmatic focusing upon entering the interior of the eye which is filled with aqueous humor. The second and third astigmatic focusings are oppositely directed and are of unequal magnitude to the first. Because the astigmatism introduced by multiple, thin concentric shells of uniform thickness (such as the walls of lens front 64 and the surface of cornea 55) is approximately zero, the total astigmatism introduced is primarily dependent upon the index of refraction of the medium inside lens body 62 and that of aqueous humor 52. Since the water 68 (in this example) filling the hollow interior of lens body 62 has an index of refraction of 1.333, which is almost the same as that of the aqueous humor (n=1.336), the combined effect of the three astigmatic focusings is almost zero.

The preferred means of fabricating the anti-astigmatic contact lens of the present application will now be described. A benefit of this fabrication scheme is that it results in a mass producible product with a near-optimal performance.

Lens body 62 of lens 61 should be molded as one piece from plastic or a plastic-like material. A suitable material would be acrylic. The plastic is preferably black in color to reduce stray light and glare. Lens front 64 is preferably an acrylic meniscus lens with an integral threaded mounting flange (not shown) around the outer edge. Lens front 64 is fitted to and forms a seal on the front of lens body 62 by means of o-ring 73. Window 66 is preferably made of glass or acrylic.

Mirrors 70 on the inside of lens 60 are preferably fabricated by depositing a multi-layer dielectric coating on a glass substrate and are designed to reflect a high proportion (over 99%) of the laser beam. The interior surface of lens body 62 can also be used as the substrate upon which the reflective coating is deposited. The external glass or acrylic surfaces of window 66 and magnification lens(es) 72 are preferably coated with multi-layer anti-reflection coatings to cause low laser and visible light reflections (less than 0.5% if possible). Finally, in the event that water or another fluid is used to fill the interior of lens body 62, a small plastic or rubber plug (not shown) in the side of lens body 62 may be used to insert fluid or remove fluid or air bubbles by means of a hypodermic needle.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

I claim:

1. A contact lens for use in delivering laser light to a region of a patient's eye and for viewing the interior of the eye during a surgical procedure, the contact lens comprising:

a hollow lens body having an entrance and an opposite exit;

a front face sealed to the exit of the lens body, the front face allowing the transmission of visible and laser light into the patient's eye and having a curvature substantially the same as the patient's eye and affixed to the lens body so that the front face can be fitted over the eye;

a window sealed to the entrance of the lens body, the window allowing the transmission of visible and laser light into the lens;

a mirrored surface on the interior of the lens body positioned so that light entering the lens from the window reflects off of the mirrored surface and exits the lens at the front face at a sufficiently steep angle to illuminate a desired region of the patient's eye; and a medium filling the lens body, the medium having an index of refraction in the range of 1.25 to 1.45.

2. The contact lens of claim 1, wherein the front face and window have thin walls and are each of substantially uniform thickness.

3. The contact lens of claim 1, wherein the lens body is fabricated from plastic.

4. The contact lens of claim 1, wherein the lens body is fabricated from metal.

5. The contact lens of claim 1, wherein the medium has an index of refraction in the range of 1.32 to 1.35.

6. The contact lens of claim 1, wherein the medium has an index of refraction substantially the same as the aqueous humor of a patient's eye.

7. The contact lens of claim 1, wherein the medium is a fluid.

8. The contact lens of claim 7, wherein the fluid is water.

9. The contact lens of claim 1, wherein the medium is a hydrophilic material.

10. The contact lens of claim 1, further comprising:

a magnifying lens positioned on the window and outside of the lens body.

11. The contact lens of claim 1, wherein the mirrored surface is fabricated from a multi-layered dielectric coating which is deposited on a glass substrate.

12. The contact lens of claim 1, wherein the mirrored surface is fabricated from a multi-layered dielectric coating which is deposited on an interior surface of the lens body.

13. The contact lens of claim 1, wherein the portions of the window external to the lens body are coated with an anti-reflection coating.

14. The contact lens of claim 10, wherein the portions of the magnifying lens not in contact with the window are coated with an anti-reflection coating.

15. A contact lens for use in delivering laser light to a region of a patient's eye and for viewing the interior of the eye during a surgical procedure, the contact lens comprising:

a hollow lens body having a front face at an exit of the lens body and a window at an opposite, entrance of the lens body, the front face allowing the transmission of visible and laser light into the patient's eye and having a curvature substantially the same as the patient's eye and oriented so that the front face can be fitted over the eye, the window allowing the transmission of visible and laser light into the lens;

a mirrored surface on the interior of the lens body positioned so that light entering the lens from the window reflects off of the mirrored surface and exits the lens at the front face at a sufficiently steep angle to illuminate a desired region of the patient's eye; and a medium filling the lens body, the medium having an index of refraction in the range of 1.25 to 1.45.

16. The contact lens of claim 15, wherein the front face and window have thin walls and are each of substantially uniform thickness.

17. The contact lens of claim 15, wherein the lens body is fabricated from plastic.

18. The contact lens of claim 15, wherein the lens body is fabricated from metal.

19. The contact lens of claim 15, wherein the medium has an index of refraction in the range of 1.32 to 1.35.

20. The contact lens of claim 15, wherein the medium has an index of refraction substantially the same as the aqueous humor of a patient's eye.

21. The contact lens of claim 15, wherein the medium is a fluid.

22. The contact lens of claim 21, wherein the fluid is water.

23. The contact lens of claim 15, wherein the medium is a hydrophilic material.

24. The contact lens of claim 15, further comprising:

a magnifying lens positioned on the window and outside of the lens body.

25. The contact lens of claim 15, wherein the mirrored surface is fabricated from a multi-layered dielectric material which is deposited on a glass substrate.

26. The contact lens of claim 15, wherein the mirrored surface is fabricated from a multi-layered dielectric coating which is deposited on an interior surface of the lens body.

27. The contact lens of claim 15, wherein the portions of the window external to the lens body are coated with an anti-reflection coating.

28. The contact lens of claim 24, wherein the portions of the magnifying lens not in contact with the window are coated with an anti-reflection coating.

* * * * *